United States Patent
Grooms et al.

[11] Patent Number: 6,090,998
[45] Date of Patent: Jul. 18, 2000

[54] SEGMENTALLY DEMINERALIZED BONE IMPLANT

[75] Inventors: Jamie M. Grooms, Alachua; Kevin C. Carter, Gainesville; Thomas W. Sander, Alachua, all of Fla.

[73] Assignee: University of Florida, Alachua, Fla.

[21] Appl. No.: 08/958,364

[22] Filed: Oct. 27, 1997

[51] Int. Cl.[7] ................ A61F 2/28; A61F 2/08; A61F 2/30
[52] U.S. Cl. ................ 623/16; 623/13; 623/18; 623/66
[58] Field of Search ................ 623/16, 13, 18, 623/21, 66; 128/898; 523/113, 115

[56] References Cited

U.S. PATENT DOCUMENTS

| | | |
|---|---|---|
| D. 277,509 | 2/1985 | Lawrence et al. . |
| D. 277,784 | 2/1985 | Scarlato et al. . |
| D. 284,099 | 6/1986 | Laporta et al. . |
| 3,772,709 | 11/1973 | Swanson . |
| 3,875,594 | 4/1975 | Swanson . |
| 3,886,600 | 6/1975 | Kahn et al. . |
| 4,627,853 | 12/1986 | Campbell et al. . |
| 4,759,768 | 7/1988 | Hermann et al. . |
| 4,871,367 | 10/1989 | Christensen et al. . |
| 4,932,973 | 6/1990 | Gendler . |
| 5,053,049 | 10/1991 | Campbell et al. . |
| 5,092,887 | 3/1992 | Gendler . |
| 5,092,896 | 3/1992 | Meuli et al. . |
| 5,133,761 | 7/1992 | Krouskop . |
| 5,171,273 | 12/1992 | Silver et al. . |
| 5,292,349 | 3/1994 | Foresti . |
| 5,405,390 | 4/1995 | O'Leary et al. . |
| 5,405,400 | 4/1995 | Linscheid et al. . |
| 5,484,443 | 1/1996 | Pascarella et al. . |
| 5,507,813 | 4/1996 | Dowd et al. . |
| 5,899,939 | 5/1999 | Boyce et al. ............ 623/16 |
| 5,919,234 | 7/1999 | Lemperle et al. . |

*Primary Examiner*—Mickey Yu
*Assistant Examiner*—Dinh X. Nguyen
*Attorney, Agent, or Firm*—Bencen & Van Dyke, P.A.; Gerard H. Bencen; Timothy H. Van Dyke

[57] ABSTRACT

This invention provides a novel unitary bone implant having at least one rigid, mineralized bone segment, which may be machined to include threads, grooves, a driver head, a recess or a symmetric or asymmetric shape, and a flexible, demineralized segment, which may also be machined to any desired shape prior to demineralization, or after demineralization. The implant of this invention has wide orthopedic applicability, including for repair or replacement of ligaments, tendons and joints.

26 Claims, 8 Drawing Sheets

3A

3B

7A

7B

7C

7D

SEGMENTALLY DEMINERALIZED BONE IMPLANT

FIELD OF THE INVENTION

This invention relates to a device made from segmentally demineralized and appropriately shaped and machined bone for implantation as a ligament, tendon, support or in any other application in which a unitary implant having a first rigid, machined segment and a second, flexible segment, is required.

BACKGROUND

There is a continuing need in the art for biologically acceptable ligament or tendon replacements. Various efforts have been made in the art to accommodate this need. For example, in U.S. Pat. No. 5,053,049, a flexible prosthesis of predetermined shape and a process for making said prosthesis was disclosed. According to that disclosure, a flexible biocompatible and non-antigenic prosthesis for replacement of a cartilaginous part was prepared by machining bone into a desired shape corresponding to the shape of a cartilaginous body part to be replaced, demineralization of the bone to impart flexibility, and tanning to reduce antigenicity. There was no disclosure or suggestion of using the demineralized bone as a tendon or ligament replacement.

In U.S. Pat. No. 5,092,887, a method for replacement or augmentation of a damaged fibrous connective tissue was disclosed wherein a ligament made from a segment of bone that had been demineralized was attached between first and second body parts. There was no disclosure or suggestion of machining the bone prior to demineralization to produce fixation ends thereon, and demineralization of only a segment of the thus machined bone to produce a flexible segment, while leaving the machined attachment ends in a fully mineralized and rigid state for fixation directly to bone adapted to receive such fixation ends. The disclosure in the U.S. Pat. No. 5,092,887 with respect to its discussion of background art and methods of demineralization of bone is hereby incorporated by reference.

SUMMARY OF THE INVENTION

This invention provides a novel unitary bone implant having at least one rigid, mineralized bone segment, which may be machined to include threads, grooves, a driver head, a recess or a symmetric or asymmetric shape, and a flexible, demineralized segment, which may also be machined to any desired shape prior to demineralization, or after demineralization.

BRIEF DESCRIPTION OF THE DRAWINGS

FIG. 1B provides a view of an alternate embodiment in which one end of the implant has a rigid fixation bone block; FIG. 1D shows an end-on view of a cannulated embodiment of the implant of this invention.

DETAILED DESCRIPTION OF THE PREFERRED EMBODIMENTS

This invention provides a biologically acceptable ligament, tendon, support or other implant for replacement of damaged ligaments, tendons, vertebral disks and the like, wherein there is a need for an implant having both a rigid machined portion or segment as well as a flexible, demineralized portion or segment. According to one embodiment of this invention, a segment of preferably cortical bone is machined into a desired shape, with at least one end being machined so as to provide a means for fixation of that end directly to a bone machined in a complementary fashion.

Figure 1:
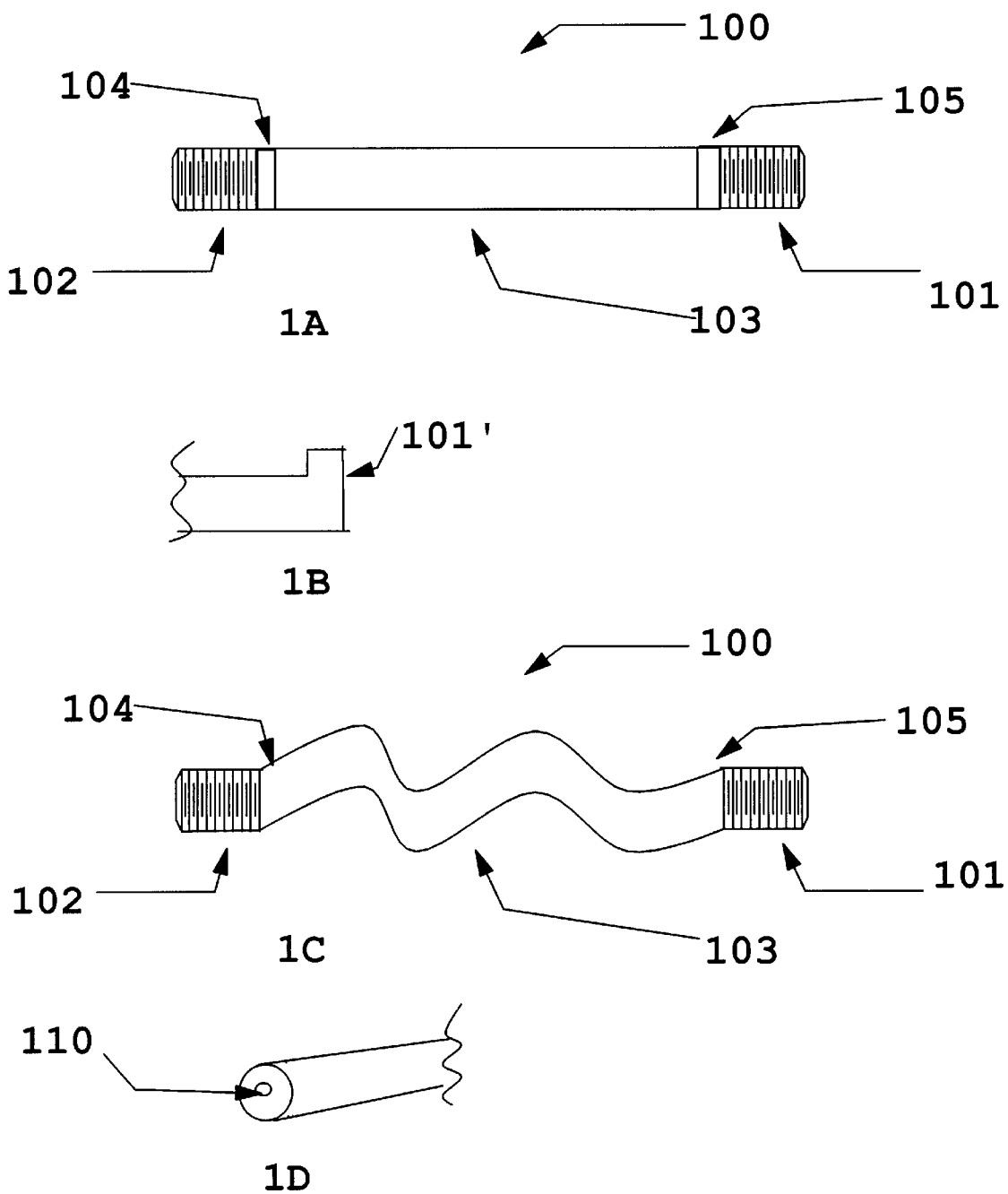
FIG. 1 provides a view of a first embodiment of the implant of this invention in which a rigid bone segment is machined to exhibit threads on each end (FIG. 1A), and which is then demineralized only in the internal section to provide a flexible segment between the machined ends (FIG. 1C)

Referring to FIG. 1A, a first embodiment of the implant of this invention 100 is shown in which the ends 101 and 102 of the implant are machined so as to exhibit a thread, and the bone to which the implant is to be affixed is tapped to exhibit a receiving thread complementary to the thread on the implant end. Alternatively, the threaded ends 101, 102 may be self-tapping, thereby eliminating the need to tap the receiving bone. A simple hole, of a diameter slightly smaller than the diameter of the threaded implant ends, may be drilled or produced by like means to receive the threaded implant end. An internal segment 103 of the implant is demineralized to provide a flexible segment of the implant, while transition zones 104, 105 are provided wherein the level of mineralization of the bone gradually changes from a fully mineralized to a demineralized state. In a preferred version of this embodiment of the invention, the two ends 101, 102 of the implant are machined to exhibit threads such that clockwise or counterclockwise rotation of the entire implant results in simultaneous insertion of both ends of the implant or extraction of both ends of the implant into or out of complementarily machined bones to which the implant is to be affixed, without kinking of the flexible segment 103 of the implant. In FIG. 1B, an alternate embodiment is shown wherein one of the ends, 101', is not threaded, but is machined to any desirable shape, such as a fixation block, such that the threaded end 102 may be threaded into the receiving bone, while the fixation block 101' is affixed in place by interference screws or like means known in the art. In yet a further embodiment, shown in FIG. 1D, the entire implant is machined so as to exhibit a cannulation 110 throughout its length or a portion thereof. In this fashion, the implant may be inserted over a guide-wire or like guide means. Alternatively, the aspect 110 may be an internal thread capable of receiving a threaded retention screw. It will be recognized that features disclosed for this embodiment or any of the other embodiments of the invention may be applied to other embodiments of this invention, to produce embodiments exhibiting a variety of combinations of different features disclosed for each of the individually disclosed embodiments.

Figure 2:
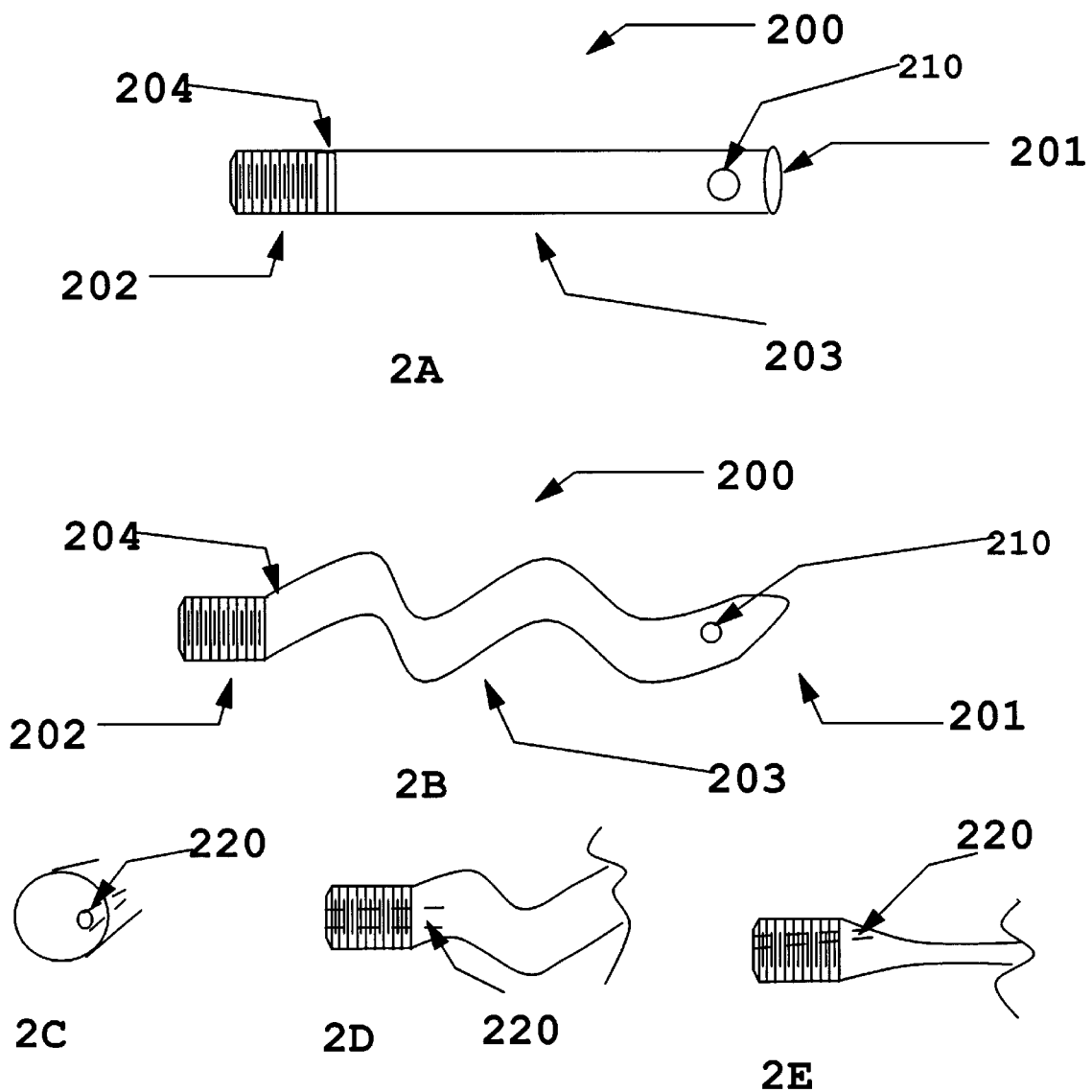
FIG. 2 provides a view of a second embodiment of the implant of this invention in which a rigid bone segment is machined to exhibit threads on one end and an attachment hole at the other (FIG. 2A), and which is then demineralized on the attachment hole end of the implant to provide a flexible segment, while retaining the threaded segment as a rigid member (FIG. 2B). A partial cannulation of the implant is shown in end-on (FIG. 2C), top (FIG. 2D) and side views (FIG. 2E).

In a further embodiment of this invention 200 shown in FIG. 2, only one end 202 of the implant 200 is machined to exhibit a thread or another machined feature, while the other end 201 may be machined to exhibit a fixation hole 210 or a similar feature, which permits for suturing or otherwise fixing that end to a ligament or a tendon. A transition zone 204 from a mineralized to a demineralized state is provided, as is a flexible segment of the implant 203. In FIGS. 2C–E, there are shown an end-on view, a side view and a top view, respectively. In this embodiment of the invention, an optional cannulation 220 is shown, permitting threading of the machined portion 202 of the implant over a guide-wire, for example, while not interfering with the flat, demineralized segment 203 of the implant.

Figure 3:
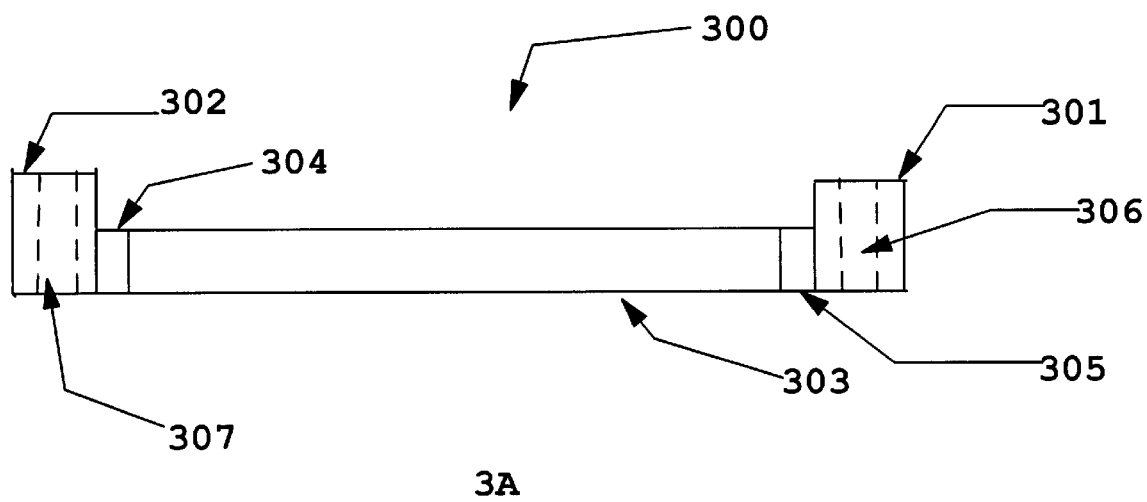
FIG. 3 provides a view of a third embodiment of the implant of this invention in which a rigid bone segment is machined to exhibit a fixation block at each end of the implant (FIG. 3A), and which is then demineralized between the two ends to provide a flexible segment between the machined fixation block ends (FIG. 3B).
Figure 3:
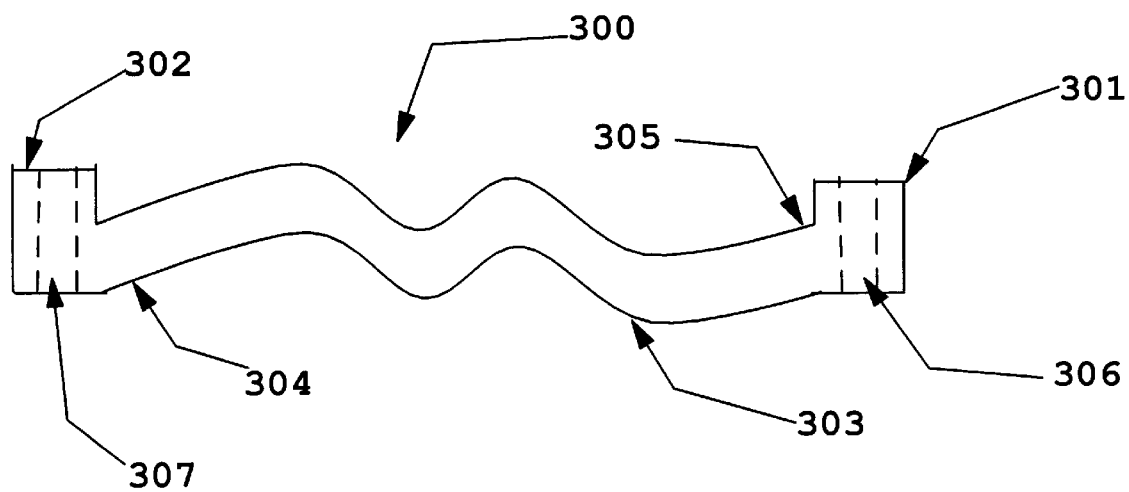

In a further embodiment 300 of this invention shown in FIG. 3, the implant may be used to replace a ligament. In this embodiment, two transition zones 304, 305 from the flexible segment 303 to terminally mineralized fixation blocks 301, 302 are provided. The fixation blocks 301 and 302 each have a canal 306, 307 machined therein for receiving a fixation screw or pin. The mineralized sections 302, 303 may be machined into any desired form of an anchoring fixture. The anchoring fixture may contain a screw thread, a hole for receipt of an anchoring pin or an anchoring screw, or a screw that rotates within a sleeve.

Figure 4:
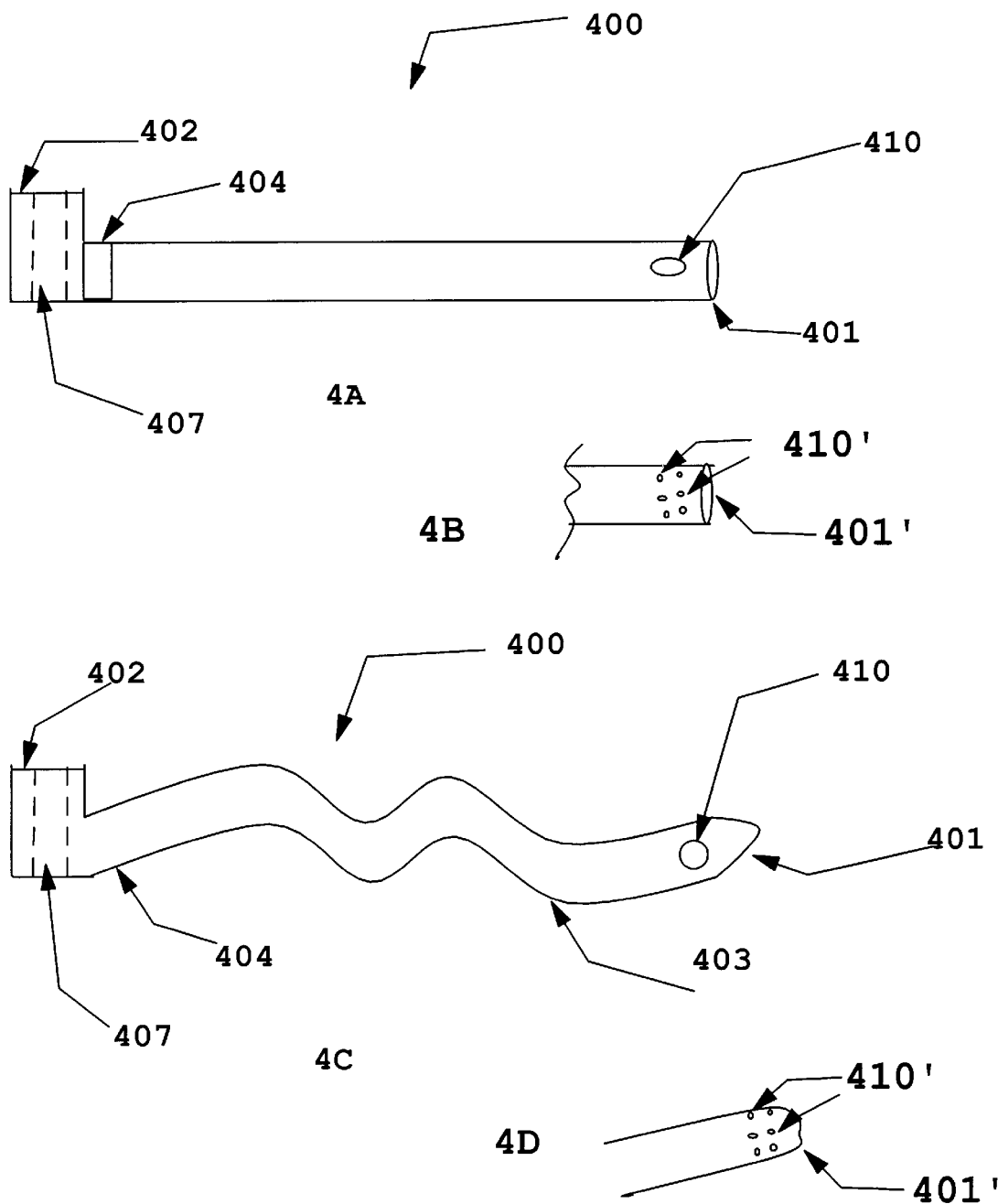
FIG. 4 provides a view of a fourth embodiment of the implant of this invention in which a rigid bone segment is machined to exhibit a fixation block at one end and an attachment hole (FIG. 4A) or several holes or perforations (FIG. 4B) at the other, and which is then demineralized at the end bearing the attachment hole(s) (FIGS. 4C and 4D) to provide a flexible segment, while retaining the fixation block end as a rigid member.

In the embodiment 400 shown in FIG. 4A, the implant is used for repair or replacement of a tendon. In this embodiment, only one end 402 of the implant 400 is machined for fixation in a bone, and the second end 401 of the implant is adapted to a variety of shapes, terminating in a means, such as a threadable hole 410, for fixation of that end to bone, muscle, tendon or ligament. In an alternate embodiment shown in FIGS. 4B and 4D, the end 401' is machined to exhibit a plurality of holes or perforations, 410', such that end 401' may be sutured to a receiving biological structure, such as a muscle, ligament, tendon, bone or the like.

Figure 5:
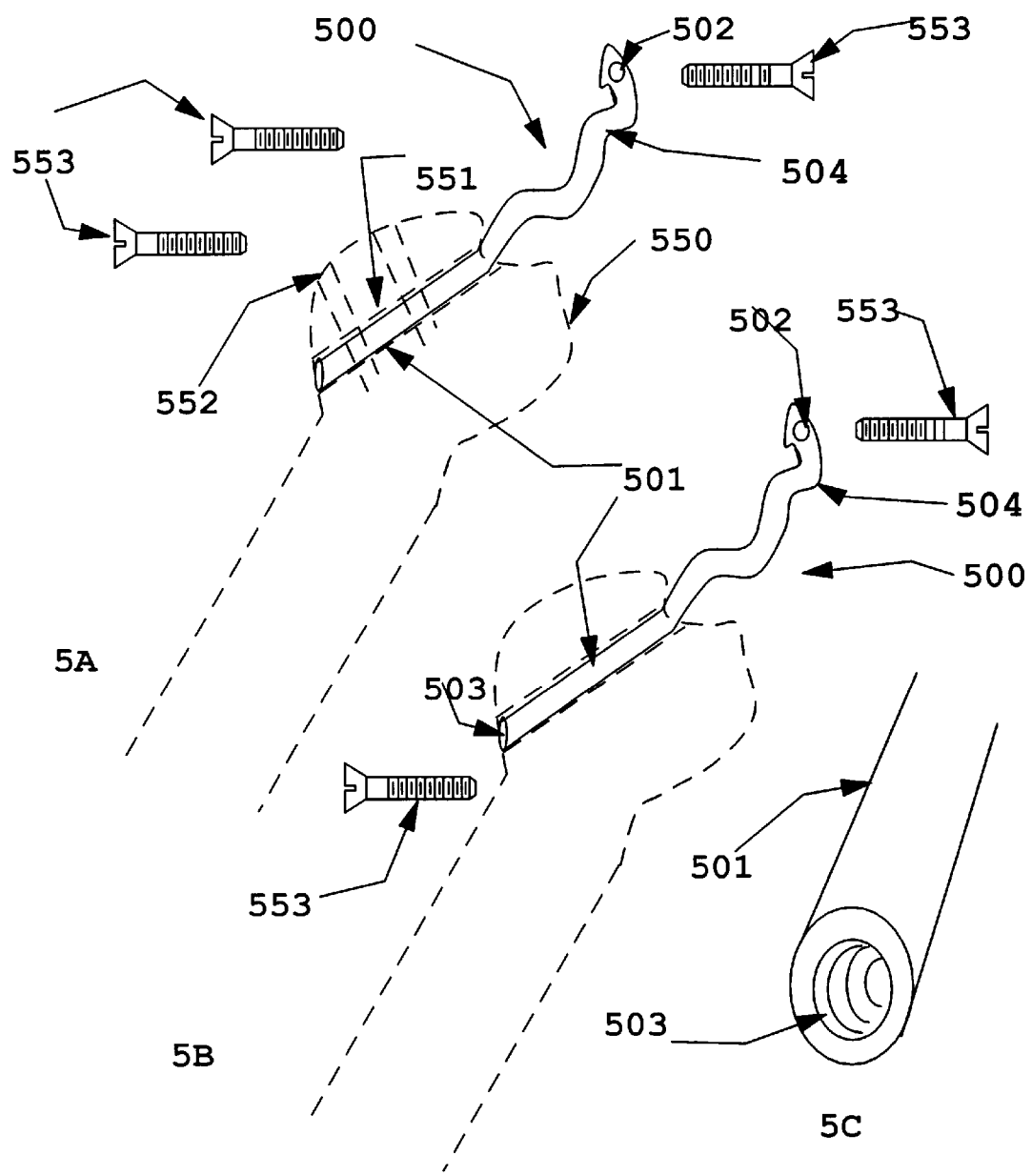
FIG. 5 shows one method of implantation of the implant of this invention in which fixation screws are utilized to retain the implant of this invention in place either by locking the implant in place through holes in the rigid segment of the implant (FIG. 5A), or by locking the implant into place at the rigid end of the implant via a tapped recess (FIGS. 5B and 5C).

In FIG. 5, one method of implantation of the implant 500 of this invention is shown in which fixation screws 553 are utilized to retain and embodiment of the implant 500 of this invention in a machined slot 551 in a bone 550 either by locking the implant in place (FIG. 5A) through holes 552 in the rigid segment 501 of the implant (FIG. 5A), or by locking the implant into place at the rigid end 503 of the implant via a tapped recess (FIGS. 5B and 5C). The other end of the implant 504 is demineralized, and is thus flexible, and terminates in a hole 502 or other fixation means by which that end of the implant is attached to bone, tendon, ligament or muscle. As noted above, section 501 could be threaded, end 502 could be retained in a mineralized state and could be shaped as a fixation block for retention by an interference screw, or threaded. In addition, the implant 500 may be cannulated, with the recess 503 continuing through the entire length of the implant, or some portion thereof.

Figure 6:
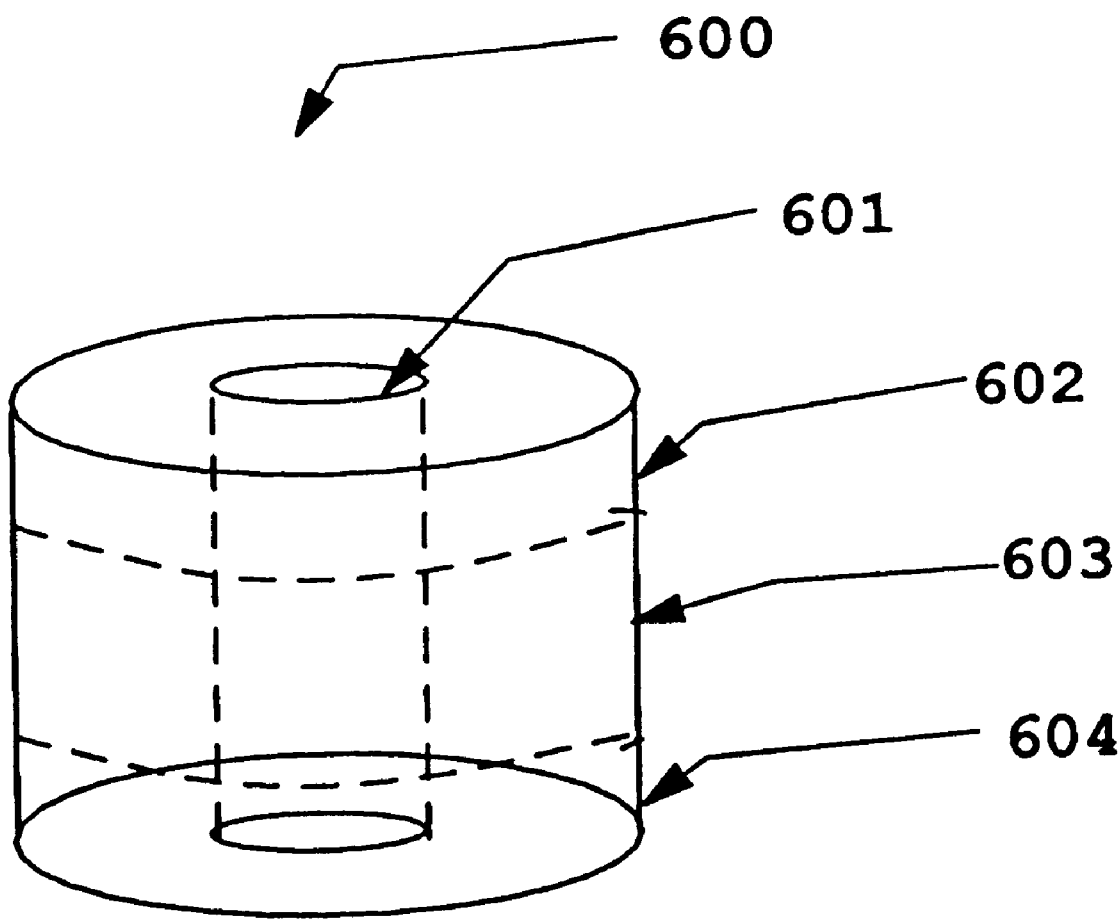
FIG. 6 shows an embodiment of this invention in which the implant is a femoral ring in which the upper and lower ends of the ring are retained in a rigid, mineralized state and which may be machined to exhibit a thread or a groove, and the internal segment of the implant is demineralized to exhibit a soft spongy layer to provide flexible support upon insertion of this embodiment of the invention between adjacent vertebral bodies.

FIG. 6 shows an embodiment of this invention in which the implant 600 is a femoral ring member in which the upper and lower ends 601, 604 are retained in a rigid, mineralized state and which may be machined to exhibit a thread or a groove by means known in the art (see WO 97/25945, hereby incorporated by reference for this purpose). The internal segment of the implant 603 is demineralized to exhibit a soft spongy region to provide flexible support upon insertion of this embodiment of the invention between, for example, adjacent vertebral bodies. An internal canal 601 is shown in the femoral ring, which derives from the natural intramedullary canal of the bone from which the femoral ring is obtained by substantially planar, parallel cross-cuts across the diaphysis of a femur or like long bone.

The implant of this invention comprising a unitary machined, segmentally demineralized bone comprising a first mineralized portion or segment, and a second, flexible, demineralized portion or segment is produced by machining a piece of preferably cortical bone into any desired shape. The bone is preferably chosen to be strong cortical bone, such as from the femur, tibia, fibula, radius or ulna. The source of the donor bone may be autograft, allograft or xenograft bone, with the appropriate cautionary steps known in the art being taken in each case to prevent introduction into the recipient of pathogenic or antigenic agents.

After appropriately shaping the implant bone stock, a segment of the implant is preferably machined to exhibit a thread or like fixation means whereby the implant may be directly affixed to recipient bone machined in a complementary fashion. That segment of the implant is retained in a mineralized state, by appropriately protecting that segment of the implant with any protective device, such as with parafilm, a rubber or latex covering, plastic wrap, and the like. The remaining segment of the implant is then demineralized according to methods known in the art. For example, in the embodiment 100 of this invention shown in FIG. 1A, both ends 101, 102 may be inserted into rubber stoppers spanning the transition zones 104, 105, and the internal segment 103, is exposed to an acid solution of sufficient strength to leach the minerals from that segment of the bone. A 5% acetic acid solution or a 1 N hydrochloric acid solution may be employed, and the implant checked periodically for the desired level of flexibility of the internal zone 103. It is important that an excessively high concentration of strong acid not be employed for this process, as this will result in cleavage of the peptide bonds of the collagenous matrix within which the minerals are deposited. Accordingly, HCl concentrations of between about 0.1N to 2N are acceptable, with the period of exposure to acid being increased for the lower acid concentrations and decreased for the higher acid concentrations. Likewise, depending on the strength of the acid used. The transition zones 104, 105 are formed by diffusion of the acid into and diffusion of the minerals out of the bone in that segment of the implant covered by the protective covering. By varying the degree of demineralization, the properties of the implant of this invention may be altered to provide optimal strength and flexibility, as required for the particular application for which the implant is to be employed.

The thus treated implant may be further treated by tanning or other means known in the art to reduce the antigenicity of the implant. For example, glutaraldehyde treatment (see U.S. Pat. No. 5,053,049, hereby incorporated by reference for this purpose), may be used.

Figure 7:
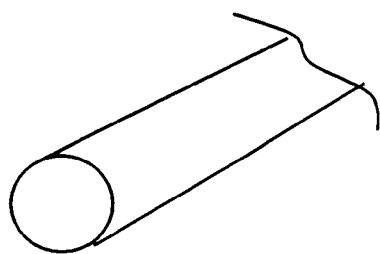
FIG. 7 shows various cross-sections for the demineralized segment of the implant of this invention.
Figure 7:
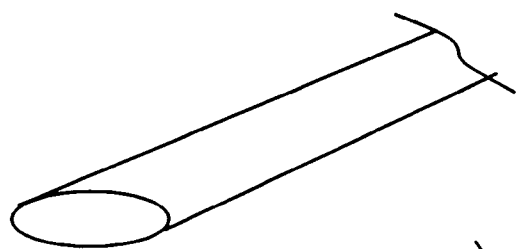
Figure 7:
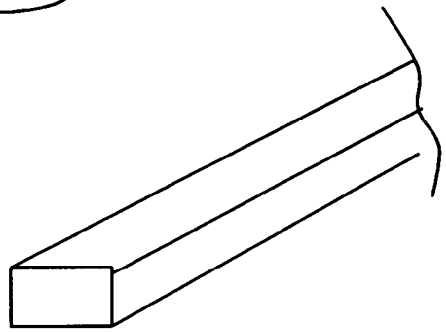
Figure 7:
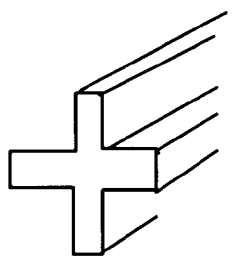

In FIG. 7, various cross-sectional shapes of the implant of this invention are shown. Thus, in FIG. 7A, a cylindrical cross-section is shown. It will be recognized that various diameters, from as small as 0.5 mm or smaller to as large as 10 mm, or in certain applications, even larger, may be desirable. In FIG. 7B, an oval cross-section is provided. In FIG. 7C, a flat cross section is provided. In FIG. 7D, a cross-shaped cross-section is provided. Those skilled in the art will recognize that the disclosure of this invention permits for essentially any desirable shape to be generated for the flexible or rigid segments of the implant of this invention, and such variations come within the scope of this disclosure and the appended claims. In forming the various cross-sectional shapes suggested herein, it is desirable that a smooth transition occurs between the rigid end(s) of the implant and the flexible segment. This is accomplished by appropriately machining the end(s) such that a taper into the flexible segment occurs, and by carefully controlling the demineralization process to ensure a graded demineralization from the fully mineralized segment to the demineralized segment.

It will further be understood from the foregoing disclosure that the implant of this invention may be appropriately fashioned for a wide diversity of applications. For example, an implant of this invention may be applied to repair of ligaments or tendons in the hand, elbow, knee, foot, ankle or any other anatomical location as needed. Furthermore, the implant of this invention may be applied to replacement any of a variety of joints. Methods and implant shapes known in the art for joint replacement, (see, for example U.S. Pat. Nos. 4,871,367; Des. 284,099; Des. 277,784; Des. 277,509; 3,886,600; 3,875,594; 3,772,709; 5,484,443; 5,092,896; 5,133,761; 5,405,400; and 4,759,768; all of which are herein incorporated by reference for their teachings of various considerations applicable to joint prosthetic implants), may be fashioned according to and replaced by the implant of the instant disclosure. Thus, in one embodiment of this invention, a piece of cortical bone is shaped so as to form a surgically implantable prosthetic joint having a load distributing flexible hinge, analogous to that disclosed in U.S. Pat. No. 3,875,594 (which was made from molded silicone rubber). According to this embodiment of the invention, a prosthesis is formed consisting of an enlarged midsection, and a pair of oppositely projecting distal and proximal stem portions. The volar aspect of the midsection is machined to exhibit an indent or transverse channel extending across its width, to form the flexible hinge upon demineralization of the midsection. The midsection, intended to act as the hinge, is demineralized, and the mineralized extremities of the implant are retained in a mineralized state for insertion of each end into the intramedullary space of the bones adjacent to the joint which the implant replaces. The mineralized extremities are machined to exhibit a thread or a ratcheting tooth structure, such that upon insertion of each end into the intramedullary space of the adjacent bones, the end is fixed in place. Since the ends are made from bone, the natural process of fusion between the implant and the bone into which it is inserted occurs over several weeks, thus permanently fixing the prosthesis into position and preventing any movement of the ends of the implant. Implants according to this embodiment of the invention may be used, for example, to replace metacarpophalangeal joints, proximal interphalangeal joints and the like. Accordingly, this invention represents a significant advance in the art as it provides a natural alternative to currently employed metallic, hydroxyapatite, silastic, silicone or like elstomeric materials for joint arthroplasty.

Figure 8:
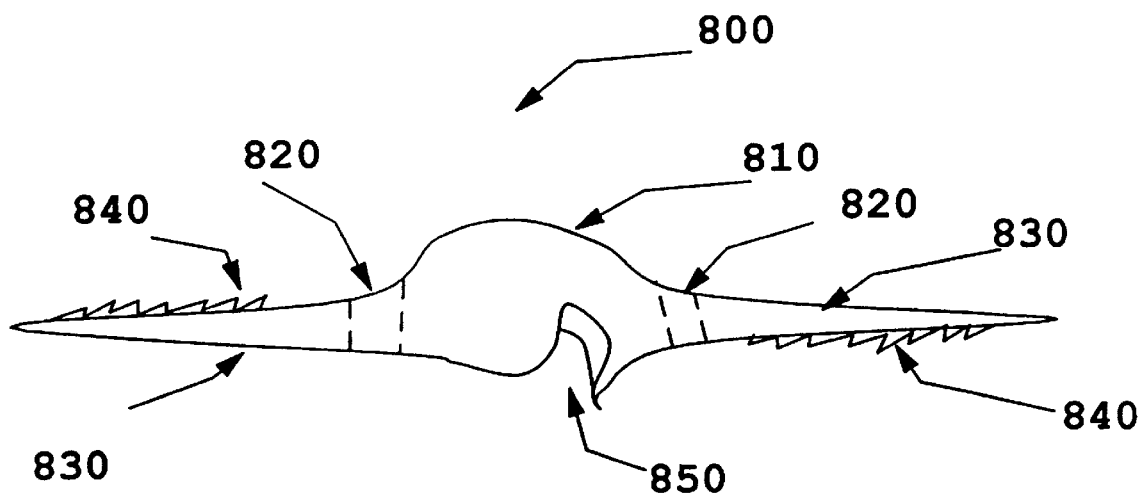
FIG. 8 depicts one embodiment of a prosthetic joint according to this invention.

In FIG. 8, there is provided one diagrammatic representation of an implant of a prosthetic joint according to this invention and which may be prepared according to the concepts central to the instant invention. The implant 800 has an enlarged midsection 810 which is demineralized up to and including a portion of the transition segment 820. On either side of the midsection 810 are mineralized projections 830 adapted for insertion into the intramedullary canals of bones adjacent to the joint which the implant 800 replaces. A groove or channel 850 is provided to act as the hinge and to allow bending motion of the joint according to principles described in U.S. Pat. No. 3,875,594, herein incorporated by reference for this purpose. Optionally, the projections 830 may exhibit an external feature designed to enhance retention of the implant in the intramedullary spaces. In the embodiment shown in FIG. 8, this feature is shown as a tooth-like serration which may be machined into an upper or lower aspect of each projection 830 or which may project around the circumference of the projections. Alternate external features which may aid in retention of the implant include holes through which retention pins may be inserted, grooves, ribbing and the like. The demineralized midsection 810 permits the implant 800 sufficient flexibility to allow that portion of the implant to act as a joint, while the projections 830 fuse with the bone into which they are inserted to form a permanent fixation.

Having now generally described various embodiments of this invention, the following examples are provided by way of further exemplification of this invention. It should be recognized that the invention disclosed and claimed herein is not to be limited to the specifics provided in these examples:

EXAMPLE 1

Machining of the Implant of this Invention

The starting bone stock was chosen such that a piece of bone consisting substantially of cortical bone was used to machine the implant of this invention. Implants from the linea aspera of the femur or an anterior aspect of the tibia were used for this purpose, but other cortical sources of bone would be acceptable. The desired bone segment was removed with a bone saw or a water-cooled diamond core cutter, and trimmed to fit in a lathe for machining of desired external features. The bone was first machined to a known diameter and length. The ends were then machined to exhibit an internal thread, an external thread, or to have one machined end while the other end of the implant was drilled to exhibit one to several holes. The internal segment destined for demineralization was then either retained in a cylindrical form or machined in a milling machine or a grinder, to exhibit a flat internal segment, or another desired shape, between the threaded ends or the fixation ends.

EXAMPLE 2

Segmental Demineralization of Machined Bone Grafts

1. Large Cylindrical Ligament Repair Grafts

Demineralization of a machined large cylindrical ligament repair graft was completed in three days using approximately 40 mL of 0.75M–1.0M hydrochloric acid solution. The implant was exposed to fresh solution at least once per day. In order to produce a gradual transition from a fully mineralized end to a fully demineralized segment, the point of contact of the HCl solution with the implant was varied over the duration of the demineralization process.

2. Small Cylindrical Ligament Repair Grafts

Demineralization of a machined small cylindrical ligament repair graft was completed in two days using approximately 40 mL of 0.75M–1.0M hydrochloric acid solution. The implant was exposed to fresh solution at least once per day. In order to produce a gradual transition from a fully mineralized end to a fully demineralized segment, the point of contact of the HCl solution with the implant was varied over the duration of the demineralization process.

3. Flat Ligament or Tendon Repair Grafts

Demineralization of a machined ligament or tendon repair graft wherein an internal segment of the graft was machined flat, was completed in twenty-four hours using approximately 40 mL of 0.75M–1.0M hydrochloric acid solution. The implant was exposed to fresh solution at least once per day. In order to produce a gradual transition from a fully mineralized end to a fully demineralized segment, the point of contact of the HCl solution with the implant was varied over the duration of the demineralization process.

4. Double Flat Ligament Repair Grafts Having Two Rigid Ends

Demineralization of a machined, flat ligament repair graft was completed in twenty-four hours using approximately 40 mL of 0.75M–1.0M hydrochloric acid solution. The implant was exposed to fresh solution at least once per day. In order to produce a gradual transition from a fully mineralized end to a fully demineralized segment, the point of contact of the HCl solution with the implant was varied over the duration of the demineralization process. In order to protect both rigid ends of the implant, one bearing a thread and the other being a fixation block, the implant was exposed to the acid solution only in the middle segment by keeping the threaded end of the implant above the meniscus of the acid, and the fixation block end of the implant was inserted into a bored-out stopper, which also acted as a plug at the bottom of the acid container, into which a hole adequate to receive the implant bearing stopper had been drilled.

In view of the foregoing disclosure and examples, in which various embodiments of the implant of this invention are disclosed and described, including the best mode, the following claims are provided to define the scope of this invention. Those skilled in the art will recognize that various modifications on the specifics of the invention disclosed herein come within the scope of the appended claims.

What is claimed is:

1. A segmentally demineralized bone implant comprising at least one mineralized segment, and at least one demineralized, flexible segment; wherein said demineralized, flexible segment is of a sufficient flexibility as to act as a ligament, tendon, or flexible support when said implant is affixed between two or more body parts.

2. The implant of claim 1 wherein said mineralized or demineralized segment is machined to exhibit a desired feature selected from a groove, an external thread, an internal thread, a driver head, a recess and a symmetric or asymmetric shape.

3. The implant of claim 2 comprising at least one machined, mineralized end or segment, adapted for fixation of said implant to or in bone.

4. The segmentally demineralized bone implant of claim 1 further comprising a zone between said mineralized segment and said demineralized segment, wherein a gradual transition from mineralized to demineralized bone occurs.

5. The segmentally demineralized bone implant of claim 2 comprising two machined, mineralized ends adapted for fixation of said implant to bone adapted to receive said machined mineralized ends of said implant, and wherein said demineralized segment extends between said two machined, mineralized ends.

6. The segmentally demineralized bone implant of claim 1 wherein said mineralized segment forms an end of the implant and which is machined to exhibit an external thread, a hole, or an internal thread, for receiving a retention screw, retention pin, sutures or threading, and wherein configured to be affixed to bone adapted to receive said machined mineralized end or said demineralized segment of said implant.

7. The segmentally demineralized bone implant of claim 4 comprising two machined, mineralized ends, wherein each said end is machined to exhibit a thread, a self-tapping thread, a hole for receipt of a retention pin or screw, or an internal thread for receipt of a retention screw, and wherein bone to which said implant is to be affixed is adapted to receive said implant.

8. The segmentally demineralized bone implant of claim 5 wherein said thread of each said end is defined such that either clockwise or counterclockwise rotation of said implant results either in simultaneous insertion of both ends into or extraction of both ends from bone adapted to receive said implant.

9. The segmentally demineralized bone implant of claim 3 wherein said at least one machined, mineralized end is adapted for fixation of said implant to bone machined in a complementary fashion, and wherein said demineralized segment having sufficient flexibility to act as a ligament or tendon terminates in a demineralized segment adapted for fixation of said demineralized segment to a bone, muscle, tendon or ligament.

10. The segmentally demineralized bone implant of claim 1, wherein said implant is configured to be affixed between a first and a second bone, between a bone and a muscle, between a bone and a tendon, or between a bone and a ligament.

11. The implant of claim 1 in the shape of a dowel or femoral ring, said implant having two cortical ends and an internal region of soft, flexible, demineralized bone.

12. The implant of claim 11 wherein a canal is present in the implant.

13. The implant of claim 11, said implant is configured to be inserted between adjacent vertebral bodies.

14. The implant of claim 1 which is cannulated throughout the implant or through a portion of the implant.

15. An improved method for the replacement or augmentation of a damaged fibrous connective tissue in a region between first and second body parts, comprising attaching an elongated artificial ligament or tendon made from demineralized bone between said first and second body parts, said artificial ligament having both compliant elasticity and high longitudinal strength such that it has sufficient flexibility to allow it to be shaped to conform to the configuration of the region to be repaired, the improvement comprising machining at least one end of the bone prior to segmental demineralization to produce at least one fixation end thereon which end is not demineralized, and demineralization of a segment of the thus machined bone to produce a flexible segment.

16. The method of claim 15 wherein said artificial ligament or tendon comprises two machined mineralized ends and an intermediate, flexible, demineralized segment.

17. A method for the replacement or augmentation of a damaged ligament or tendon comprising attaching a machined segmentally demineralized bone implant between a first and a second bone, between a bone and a ligament on a second bone, or between a bone and a tendonous segment of a muscle.

18. A method for making a tendon or ligament implant which comprises machining a segment of substantially cortical bone into any desired shape, machining at least one end thereof for fixation directly to bone, and segmentally demineralizing a segment of said substantially cortical bone such that said demineralized segment acquires sufficient flexibility and elasticity to act as a tendon or ligament replacement.

19. An implant prepared according to the method of claim 18.

20. The implant according to claim 1 comprising a flexible, demineralized midsection and two mineralized projections.

21. The implant of claim 20 wherein said mineralized projections exhibit an external feature selected from serrated edges, threads, and ribbing.

22. The segmentally demineralized bone implant according to claim 1 in the form of a prosthetic joint implant comprising cortical bone having a load distributing flexible hinge consisting of an enlarged midsection of demineralized bone, and a pair of oppositely projecting distal and proximal stem portions consisting essentially of mineralized bone.

23. The prosthetic joint of claim 22 wherein the volar aspect of said midsection is machined to exhibit an indent or transverse channel extending across its width.

24. The prosthetic joint of claim 23 wherein said oppositely projecting distal and proximal stem portions are configured to be inserted into the intramedullary space of bones adjacent to the joint which the implant replaces.

25. The prosthetic joint of claim 24 wherein said stem portions are machined to exhibit an external thread, an internal thread, a hole or series of holes to receive a retention pin or a series of retention pins, a serrated edge, or a ratcheting tooth structure, such that upon insertion of each end into the intramedullary space of the adjacent bones, the end is fixed in place.

26. A method of joint arthroplasty which comprises replacement of a metacarpophalangeal joint, a proximal interphalangeal joint, or like joint with an implant comprising a segmentally demineralized bone.

* * * * *

UNITED STATES PATENT AND TRADEMARK OFFICE
CERTIFICATE OF CORRECTION

Page 1 of 1

PATENT NO. : 6,090,998
DATED : July 18, 2000
INVENTOR(S) : Grooms et al.

It is certified that error appears in the above-identified patent and that said Letters Patent is hereby corrected as shown below:

Title page, incorrectly lists the assignee as the "University of Florida". The correct and sole assignee of this patent is the -- University of Florida Tissue Bank, Inc.--.

Signed and Sealed this

Tenth Day of July, 2001

*Attest:*

NICHOLAS P. GODICI
*Attesting Officer*    *Acting Director of the United States Patent and Trademark Office*